(12) United States Patent
Aboud (10) Patent No.: US 8,328,828 B2
(45) Date of Patent: Dec. 11, 2012

(54) DEVICE FOR PERFORMING AN ANASTOMOSIS

(75) Inventor: Emad T. Aboud, Swaida (SY)

(73) Assignee: Board of Trustees of the University of Arkansas, Little Rock, AR (US)

( * ) Notice: Subject to any disclaimer, the term of this patent is extended or adjusted under 35 U.S.C. 154(b) by 595 days.

(21) Appl. No.: 12/228,222

(22) Filed: Aug. 11, 2008

(65) Prior Publication Data

US 2010/0036398 A1 Feb. 11, 2010

(51) Int. Cl.
*A61B 17/08* (2006.01)
(52) U.S. Cl. .......................... 606/155; 606/153; 606/150
(58) Field of Classification Search .................. 606/139, 606/142, 153, 152, 155, 157, 158, 120, 205–207, 606/210–211, 150; 623/1.11, 1.23; 24/16 R
See application file for complete search history.

(56) References Cited

U.S. PATENT DOCUMENTS

| | | | | |
|---|---|---|---|---|
| 306,692 | A | * | 10/1884 | Knight ............................ 24/499 |
| 2,627,095 | A | * | 2/1953 | Palmieri .......................... 24/549 |
| 4,041,931 | A | * | 8/1977 | Elliott et al. .................. 128/899 |
| 4,765,335 | A | | 8/1988 | Schmidt et al. |
| 4,771,775 | A | * | 9/1988 | Walsh et al. ................... 606/153 |
| 4,777,949 | A | * | 10/1988 | Perlin ............................ 606/158 |
| 4,787,386 | A | * | 11/1988 | Walsh et al. ................... 606/153 |
| 4,961,743 | A | * | 10/1990 | Kees et al. ..................... 606/158 |
| 5,053,045 | A | * | 10/1991 | Schmidt et al. ............... 606/157 |
| 5,059,211 | A | | 10/1991 | Stack et al. |
| 5,380,290 | A | | 1/1995 | Makower et al. |
| 5,443,497 | A | | 8/1995 | Venbrux |
| 5,653,744 | A | | 8/1997 | Khouri |
| 5,843,170 | A | | 12/1998 | Ahn |
| 6,019,788 | A | | 2/2000 | Butters et al. |
| 6,110,188 | A | | 8/2000 | Narciso, Jr. |
| 6,123,682 | A | | 9/2000 | Knudson et al. |
| 6,371,965 | B2 | | 4/2002 | Gifford, III et al. |
| 6,402,767 | B1 | | 6/2002 | Nash et al. |

(Continued)

FOREIGN PATENT DOCUMENTS

WO WO 01/15618 A2 3/2001
(Continued)

OTHER PUBLICATIONS

Office Action, U.S. Appl. No. 12/583,423, Mar. 12, 2012.

*Primary Examiner* — Corrine M McDermott
*Assistant Examiner* — Todd J Scherbel
(74) *Attorney, Agent, or Firm* — Ray F. Cox, Jr.; Richard Blakely Glasgow (57) ABSTRACT

A vascular clip for use in end-to-side anastomoses having a handle connected to a lower ring and an upper ring. The handle includes a resilient element biasing the two rings together so that the rings are closely juxtaposed when the clip is closed. The respective facing surfaces of each of the rings may be provided with a rough surface. A graft vessel or an artificial aneurysm may be sutured to the lower ring. The graft vessel or artificial aneurysm may be autologous or heterologous material or may be made of synthetic material. The handle may fit into a clip applier that facilitates the application of the clip. The handle and the clip applier may be of different shapes depending on the various applications of the clip.

15 Claims, 14 Drawing Sheets

U.S. PATENT DOCUMENTS

| | | |
|---|---|---|
| 6,485,513 B1 | 11/2002 | Fan |
| 6,491,707 B2 | 12/2002 | Makower et al. |
| 6,596,003 B1 | 7/2003 | Realyvasquez, Jr. et al. |
| 6,652,545 B2 * | 11/2003 | Shipp et al. .................. 606/157 |
| 6,709,442 B2 | 3/2004 | Miller et al. |
| 6,743,243 B1 | 6/2004 | Roy et al. |
| 6,960,219 B2 | 11/2005 | Grudem et al. |
| 7,141,060 B1 | 11/2006 | Metz et al. |
| 7,220,268 B2 | 5/2007 | Blatter |
| 2004/0215220 A1 | 10/2004 | Dolan et al. |
| 2005/0149077 A1 * | 7/2005 | Gifford et al. ............... 606/153 |
| 2005/0182483 A1 | 8/2005 | Osborne et al. |
| 2006/0282106 A1 * | 12/2006 | Cole et al. .................... 606/153 |
| 2008/0045985 A1 * | 2/2008 | Gurtner et al. ............... 606/154 |
| 2008/0195125 A1 * | 8/2008 | Hoffman ....................... 606/153 |
| 2010/0122698 A1 | 5/2010 | Shaffer et al. |

FOREIGN PATENT DOCUMENTS

| | | |
|---|---|---|
| WO | WO 02/096298 | 12/2002 |
| WO | WO 02/098303 A1 | 12/2002 |
| WO | WO 03/007843 | 1/2003 |

* cited by examiner

DEVICE FOR PERFORMING AN ANASTOMOSIS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to devices for vascular anastomosis, and in particular, to devices for end-to-side vascular anastomoses.

2. Brief Description of the Related Art

Devices for assisting in vascular anastomosis are known but most of them are complicated and have more than one part which makes the anastomosis more complicated to perform.

The limitations of the prior art are overcome by the present invention as described below.

BRIEF SUMMARY OF THE INVENTION

The present invention is a clip made of metal or similar materials for use in end-to-side anastomoses, i.e., in connecting the end of a homogeneous graft vessel or artificial graft to the side of a recipient vessel in different parts of a human or animal body. The clip comprises a handle and two rings, a lower ring and an upper ring. The two rings are closely juxtaposed when the clip is closed. The handle may be similar to but smaller than the aneurysm dips known in the art, for example, the aneurysm clip disclosed in U.S. Pat. No. 4,765,335, the disclosure of which is incorporated herein in its entirety.

The handle may fit into a clip applier that facilitates the application of the clip as described below. The handle and the clip applier may be of different shapes depending on the various applications of the dip.

The rings may also have different shapes and sizes to accommodate different kinds of anastomoses and different vessels of all sizes in all parts and cavities of the human or animal body, including without limitation the brain, thorax, abdomen, pelvis, neck and limbs. The rings may be of various shapes, including but not limited to circular or elliptical. When the clip is used with small vessels, for example in cerebrovascular anastomoses within the skull, it is desirable that the size of the lower ring and the handle be as thin as possible.

To ensure a firm grasp of the rings on the vessel walls, the inner surface of each of the rings, i.e., the surface facing the other ring, may be provided with a rough surface or the surface of one ring may be provided with spines that fit into holes in the facing surface of the other ring. The handle may additionally urge the two rings together by, for example, a resilient element such as a spring.

The clip of the present invention has a wide range of uses all over the body. The present invention also has the benefits of shortening surgery time and minimizing occlusion time during regular anastomoses as compared to using other complicated devices known in the prior art. The different sizes and shapes of the clip widen the range of its use. In addition the embodiment of the clip incorporating a graft vessel made of synthetic material will provide the vascular surgeon with a wide range of choices making it a benefit to vascular surgery. As compared to the prior art, the present invention is simpler, easier to use, composed of one piece, and it can be used on vessels of 2 mm up to the largest vessels in the body.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWING

FIGS. 12-15 are views of an embodiment of the present invention being employed to attach a graft vessel to a recipient vessel.

DETAILED DESCRIPTION OF THE INVENTION

With reference to FIGS. 1-22, the preferred embodiment of the present invention may be described as follows.

The present invention is a clip for use in end-to-side anastomoses, i.e., in connecting the end of a graft vessel to the side of a recipient vessel in different parts of a human or animal body. As shown in FIGS. 1-4, the clip 10 comprises a handle 11 to which two rings, a lower ring 12 and an upper ring 13, are attached. The two rings 12, 13 are closely juxtaposed when the clip 10 is closed. The handle 11 may be similar to but smaller than the aneurysm clips known in the art, for example, the aneurysm clip disclosed in U.S. Pat. No. 4,765,335, the disclosure of which is incorporated herein in its entirety.

Figure 1:
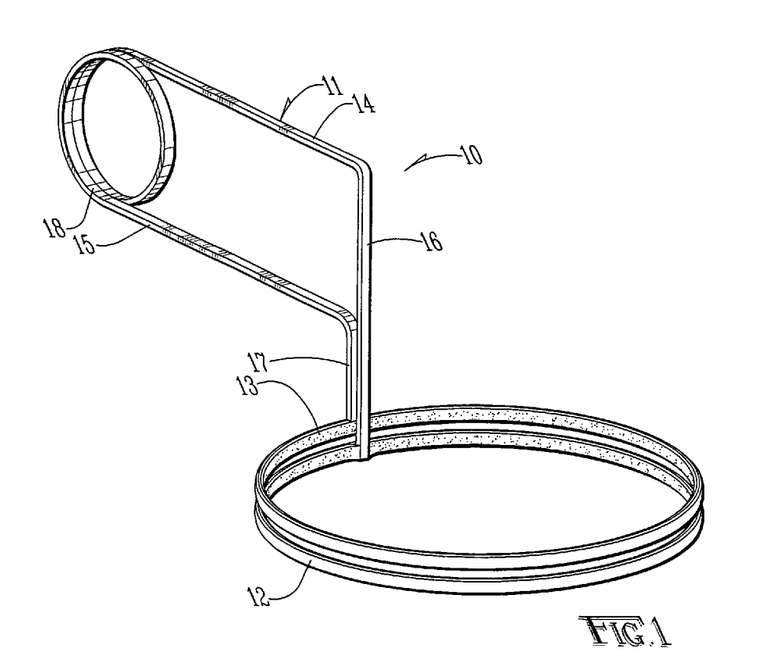
FIG. 1 is a perspective view of one embodiment of the present invention in which the clip is formed from a single length of wire and a resilient element in the form of a coil spring is formed into the handle of the clip.
Figure 2:
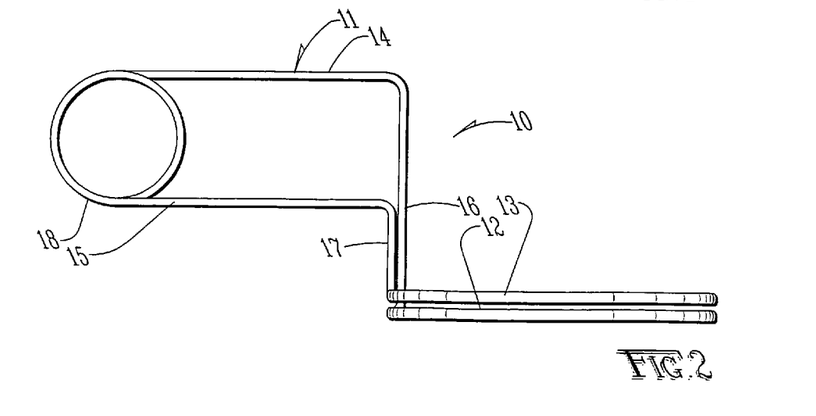
FIG. 2 is a right side elevation view of the embodiment of FIG. 1.
Figure 3:
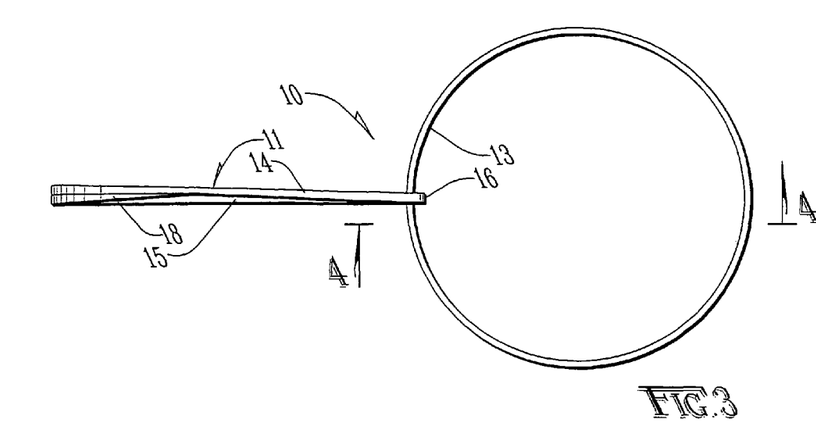
FIG. 3 is a top plan view of the embodiment of FIG. 1.
Figure 4:
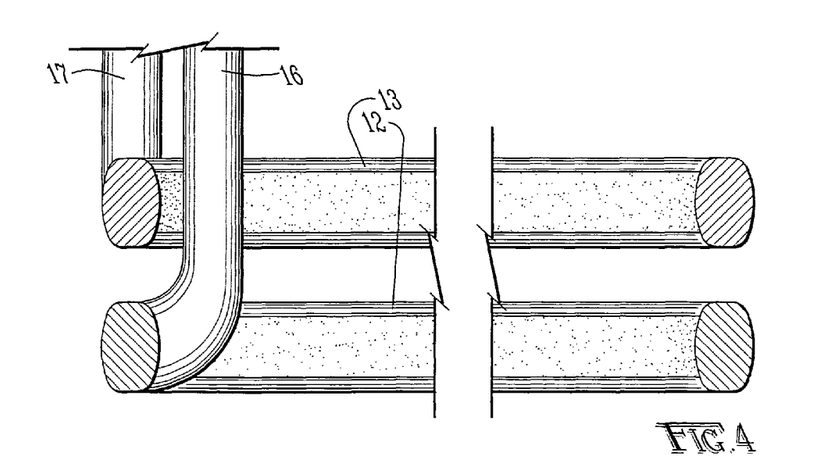
FIG. 4 is a cross sectional detail of the relationships among the rings and the offset segments taken along the line 4-4 of FIG. 3.

The clip 10 may be formed as shown in FIG. 1 from a single segment of material, such as by bending and forming a metal wire, or it may be formed in several pieces as will be described below. A preferred metal for constructing the clip 10 is titanium or any bio-compatible metal. It will be desirable in some applications that the material from which the clip 10 is made is compatible with medical imaging devices, such as MRI's. In surgical training applications where the clip 10 is used with a cadaver model, the clip 10 may be made of plastic or the like.

The handle 11 may additionally incorporate means to urge the two rings 12, 13 together by, for example, a resilient element such as a spring. The clip 10 may itself be made of a resilient material, such as an elastic metal, that may also incorporate a resilient element such as a coil spring. In the embodiment shown in FIG. 1, the handle 11 comprises a first arm 14 and a second arm 15. The first arm 14 is connected by a first offset segment 16 to the lower ring 12. As shown in FIGS. 1-4, and particularly in FIG. 4, the first offset segment 16 is disposed to pass to the inside of the upper ring 13. The first offset segment 16 may in one embodiment be substantially perpendicular to said first arm 14 and to said lower ring 12. The second arm 15 is connected by a second offset segment 17 to the upper ring 13. The second offset segment 17 may in one embodiment be substantially perpendicular to said second arm 15 and to said upper ring 13. In other embodiments, the offset may be obtained by various combinations of straight and curved segments as desirable for various applications. Offsetting the main axis of the handle 11 from the plane containing the rings 12, 13 allows the lower ring 12 to be placed into an arteriotomy of a recipient vessel as described below while maintaining the handle 11 spaced apart from the recipient vessel for ease of manipulation of the handle 11. The two arms 14, 15 are connected by an integral coil spring 18 disposed so as to bias the two arms 14, 15 apart and therefore to bias the two rings 12, 13 together. However, by applying pressure urging the two arms 14, 15 together, the rings 12, 13 may be separated against the biasing force of the coil spring 18. The embodiment of FIGS. 1-4 may be formed integrally from a single segment of resilient material, such as a metal wire.

Figure 18:
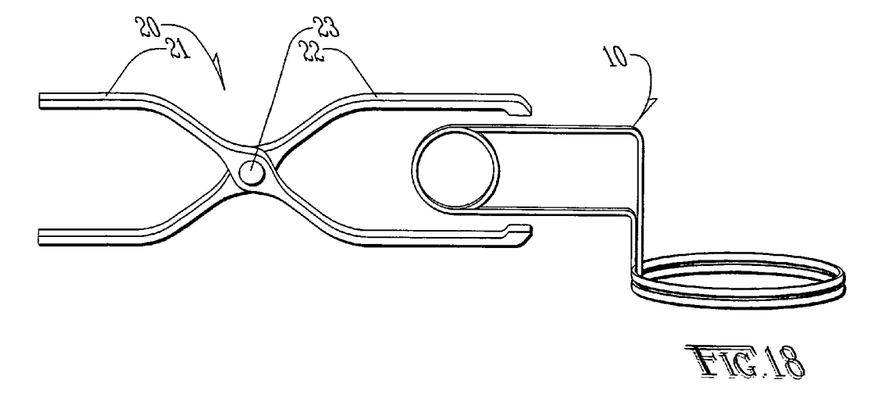
FIGS. 18-19 are elevation views of two embodiments of a clip applier.
Figure 19:
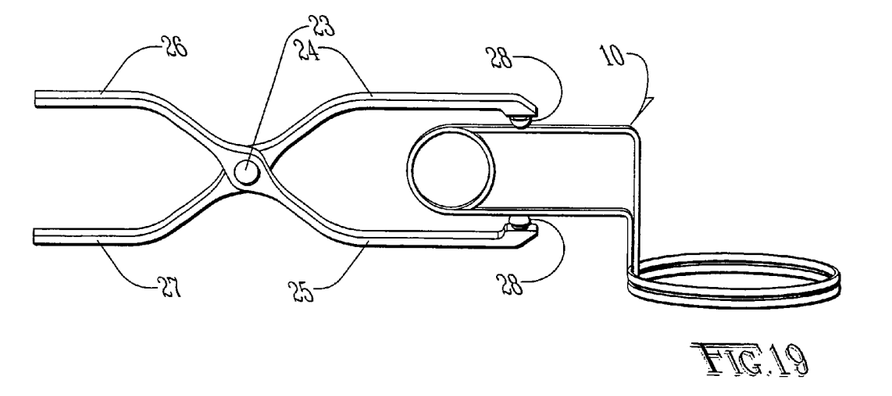

As shown in FIG. 18, the force to separate the two rings 12, 13 may be applied by a clip applier 20 to the arms 14, 15. (The figures only illustrate the tip of the clip applier and not the entire clip applier, which would be known to those of skill in the art.) The clip applier 20 may comprise a pair of members 21, 22 pivotally connected about a hinge joint 23. Each of said members 21, 22 comprises a jaw 25, 24 respectively, disposed anteriorly of said hinge joint 23 and a grip 26, 27 respectively, disposed posteriorly of said hinge joint 23 so that when the grips 26, 27 are manually closed, the jaws 25, 24 may be positioned to close onto the handles 14, 15 to urge the rings 13, 12 apart. The jaws 25, 24 may be curved as shown in FIG. 18 or, as shown in FIG. 19, the jaws 25, 24 may optionally be provided with buttons 28 on the interior faces of the jaws 25, 24 to act as low friction pivot points between the jaws 25, 24 and the arms 31, 32.

Figures 10, 11:
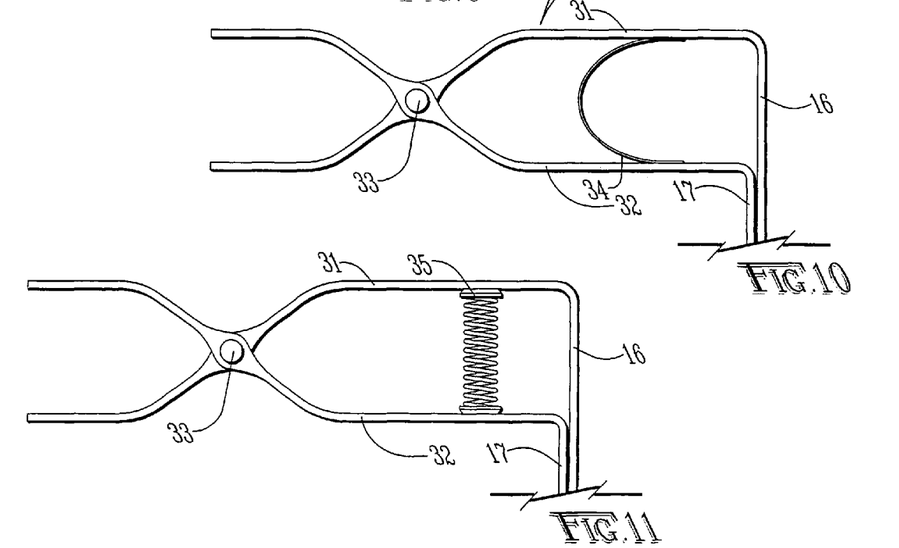
FIG. 10 is an elevation view of an alternative embodiment in which the two arms of the handle are pivotally connected.
FIG. 11 is an elevation view of an alternative embodiment having pivotally connected arms as shown in FIG. 10 and a coil spring between the arms as shown in FIG. 9.

As illustrated in an alternative embodiment in FIG. 10, the clip 30 is made with two pivotal arms 31, 32 which are pivotally connected at a pivot point 33. The first pivotal arm 31 is connected to the first offset segment 16 and thence to the lower ring 12. The second pivotal arm 32 is connected to the second offset segment 17 and thence to the upper ring 13.

Figures 8, 9:
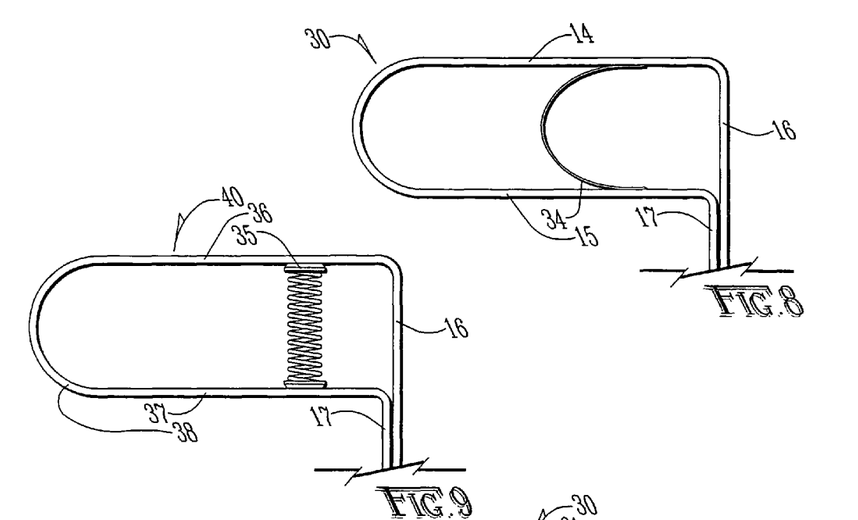
FIG. 8 is an elevation view of an alternative embodiment of the present invention in which a resilient element in the form of a segment of elastic material is disposed between the arms of the handle.
FIG. 9 is an elevation view of an alternative embodiment in which the clip is formed from a single length of wire with the two arms of the handle connected by a simple half circle. A resilient element in the form of a coil spring is disposed between the arms of the handle.
Figure 14:
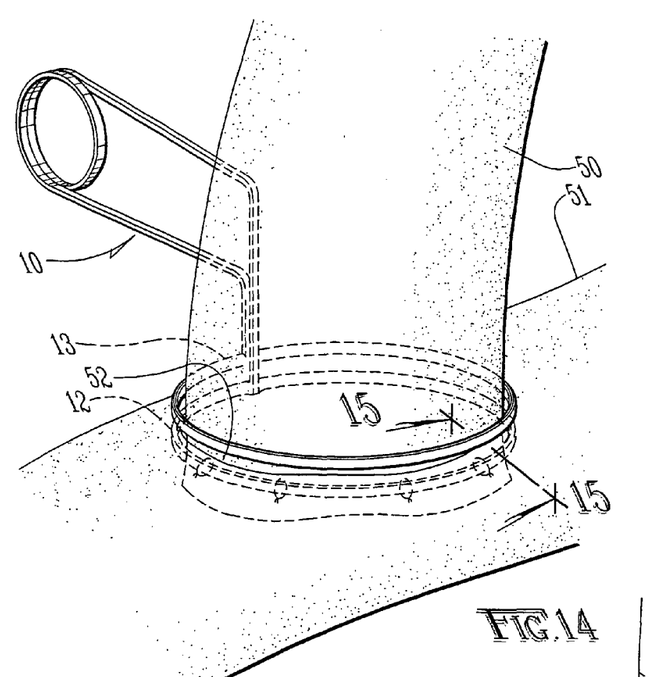
Figure 15:
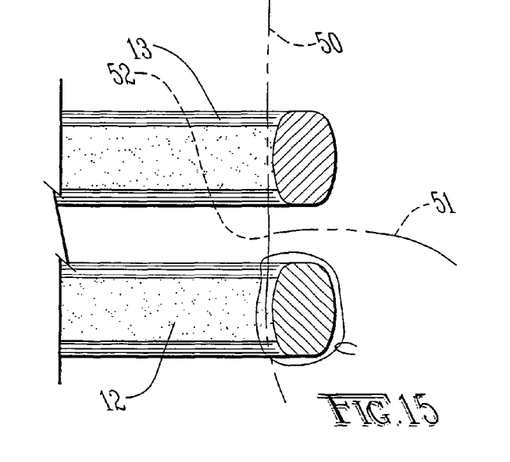
FIG. 15 is a cross sectional detail along the line 15-15 of FIG. 14.

The resilient element that urges the upper ring 13 and the lower ring 12 together may have various forms other than the integral coil spring 18 shown in FIG. 14. For example, FIGS. 8 and 10 illustrate an alternative embodiment in which the resilient element is a segment of resilient material 34 disposed between the arms 14, 15 or 31, 32. In the embodiments of FIGS. 9 and 11, the resilient element is a separate coil spring 35 disposed between the arms 31, 32 or 36, 37. In the embodiment of FIG. 9, the arms 36, 37 are connected together by a resilient arc 38. With the exception of the separate coil spring 35, the clip 40 of FIG. 9 may be formed integrally from a single segment of resilient material, such as a metal wire.

FIG. 11 illustrates an alternative embodiment having pivotally connected arms 31, 32 as shown in FIG. 10 and a separate coil spring 35 between the arms 31, 32 as shown in FIG. 9.

Figures 21A, 21B:
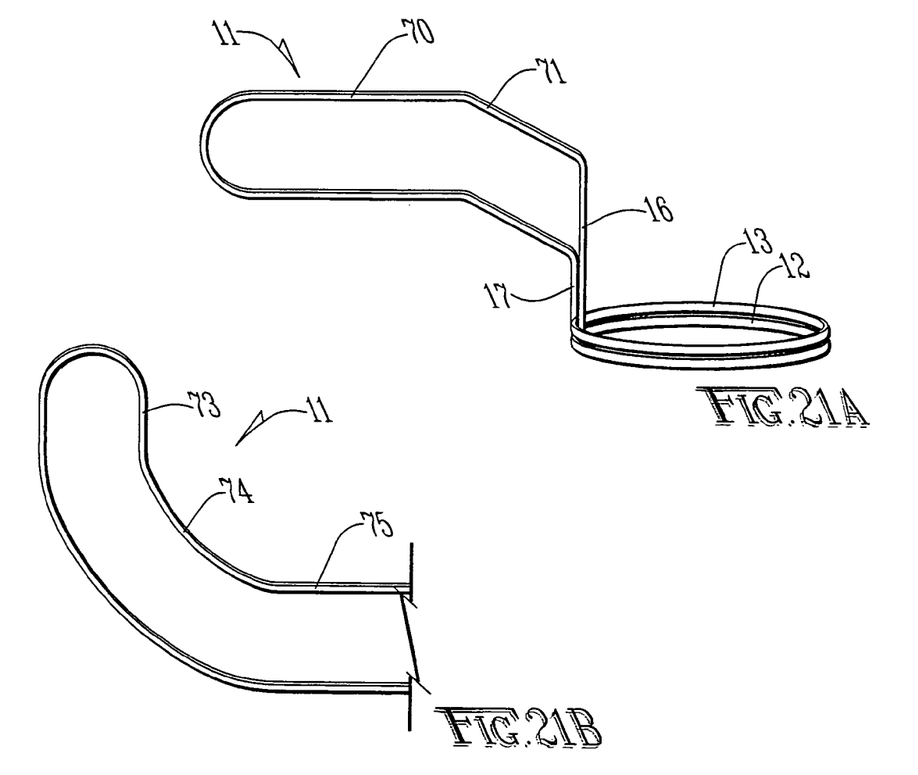
FIGS. 21A-E are elevation views of various embodiments of the handle.
Figure 21C:
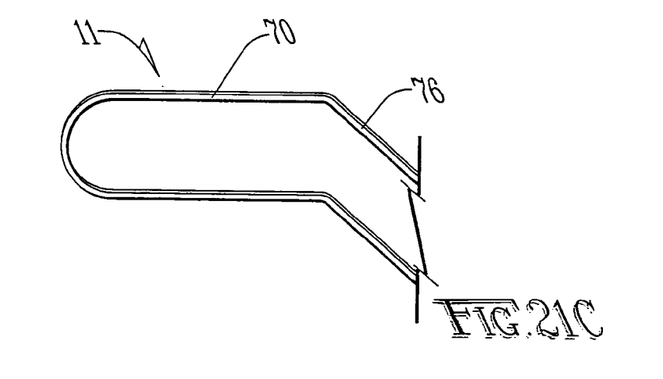
Figure 21D:
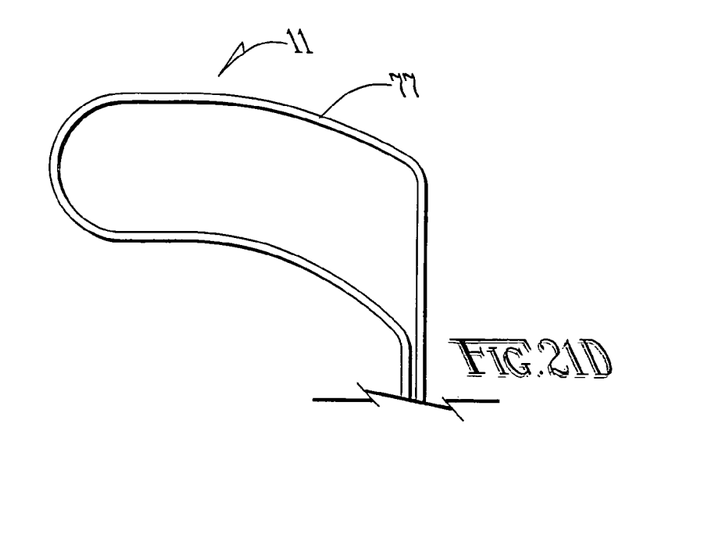
Figure 21E:
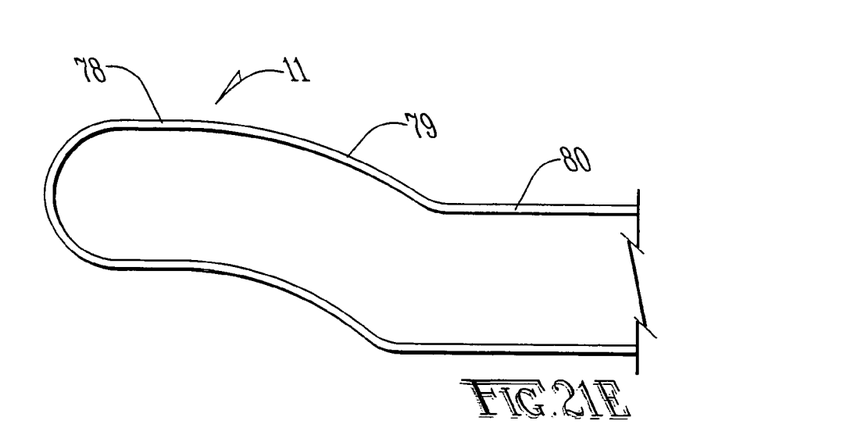

The handle 11 may be of different shapes depending on the various applications of the clip 10. For example, the handle 11 may include various combinations of straight and curved segments to accommodate various applications. For example, in FIG. 21A, the handle 11 includes a straight segment 71 disposed substantially parallel to the plane of the rings 13, 12 and operatively connected to the offset segments 16, 17 by an oblique downwardly angled straight segment 71. FIG. 21B shows an alternative embodiment of the handle 11 having a straight segment 73 disposed substantially perpendicular to the plane of the rings 13, 12 and connected first to a concavely curving segment 74 and thence to a straight segment 75 substantially parallel to the plane of the rings 13, 12. The straight segment 75 then connects to the offset segments 17, 16 (not shown) as described heretofore. FIG. 21C is an embodiment similar to that of FIG. 21A having an oblique straight segment 70, but with a more sharply downwardly angled segment 76. Oblique angles around 45° from the vertical are preferred. FIG. 21D shows a handle 11 that comprises a curved segment 77 that is curved along substantially its entire length. FIG. 21E shows a handle 11 that includes a substantially straight segment 78 that is disposed substantially parallel to the plane of the rings 12, 13 as heretofore described in reference to FIGS. 21A and 21C. The straight segment 78 is connected to a convexly curved segment 79 and thence to a second straight segment 80. The embodiments of FIGS. 21A-E are illustrative only and are not limiting to the full scope of the invention which may include various other shapes of handles to accommodate any applications for a vascular clip as would be apparent to one of skill in the art.

Figure 5:
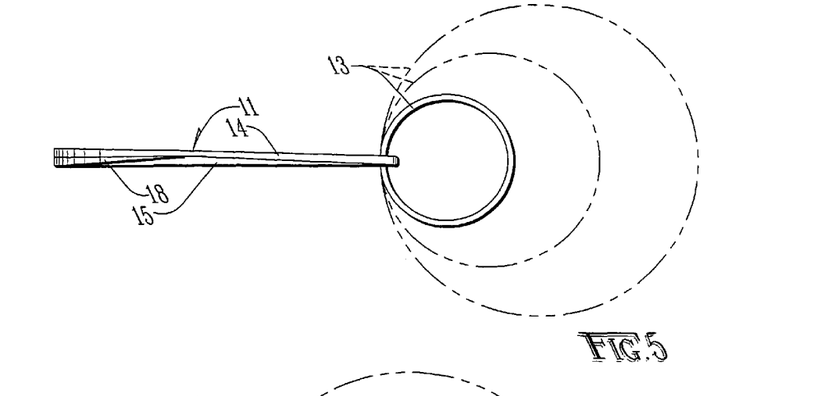
FIG. 5 is a top plan view of an embodiment of the present invention illustrating in phantom outline various sizes of substantially circular rings.
Figure 6:
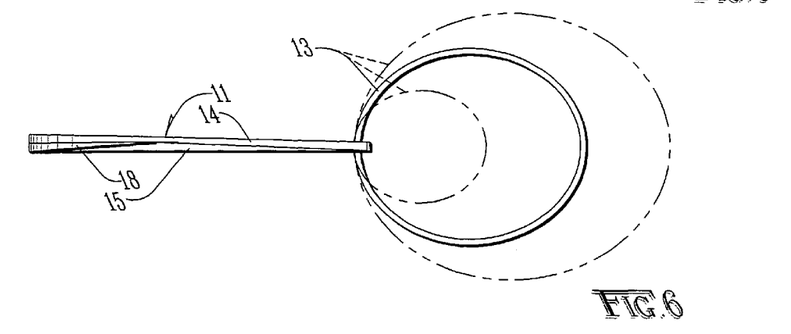
FIG. 6 is a top plan view of an embodiment of the present invention illustrating in phantom outline various sizes of wide elliptical rings.
Figure 7:
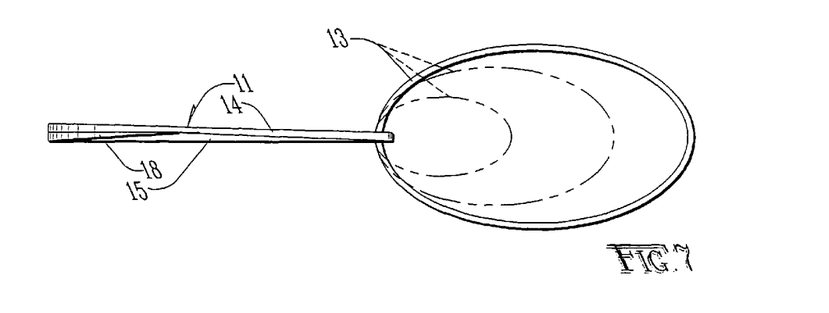
FIG. 7 is a top plan view of an embodiment of the present invention illustrating in phantom outline various sizes of narrow elliptical rings.

As shown in FIGS. 5-7, the rings 13, 12 may also have different shapes and sizes to accommodate different kinds of anastomoses and different vessels of all sizes in all parts and cavities of the human or animal body, including without limitation the brain, thorax, abdomen, pelvis, neck and limbs.

FIG. 5 illustrates rings 13 that are substantially circular in varying sizes from large to small. Likewise, FIG. 6 illustrates rings 13 with an broad elliptical shape and FIG. 7 illustrates rings 13 with narrower elliptical shape. Although the lower ring 12 is not shown in FIG. 5-7, the two rings 12, 13 are preferably substantially the same shape and size. The rings 12, 13 may have a maximum dimension (for example, a diameter in the case of a circular shape or a major axis in the case of an elliptical shape), which preferably is in the range of from around 2 mm up to around 2.5 cm, although the present invention is not limited to this size range. When the clip is used with small vessels, for example in cerebrovascular anastomoses within the skull, it is desirable that the size of the lower ring 12 and the handle 11 be as thin as possible.

Figure 12:
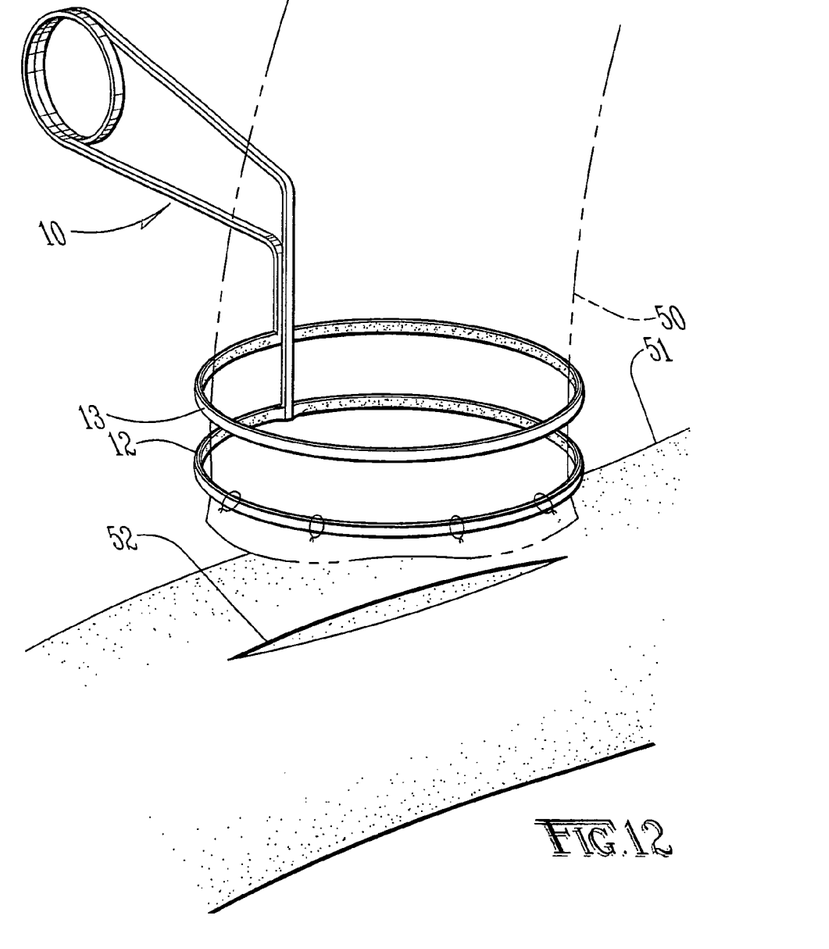
FIGS. 12-14 are perspective views showing the graft vessel sutured to the lower ring (FIG. 12), the rings opened to allow the lower ring to be inserted into an arteriotomy in the recipient vessel (FIG. 13) and the rings closed to complete the anastomosis (FIG. 14).
Figure 13:
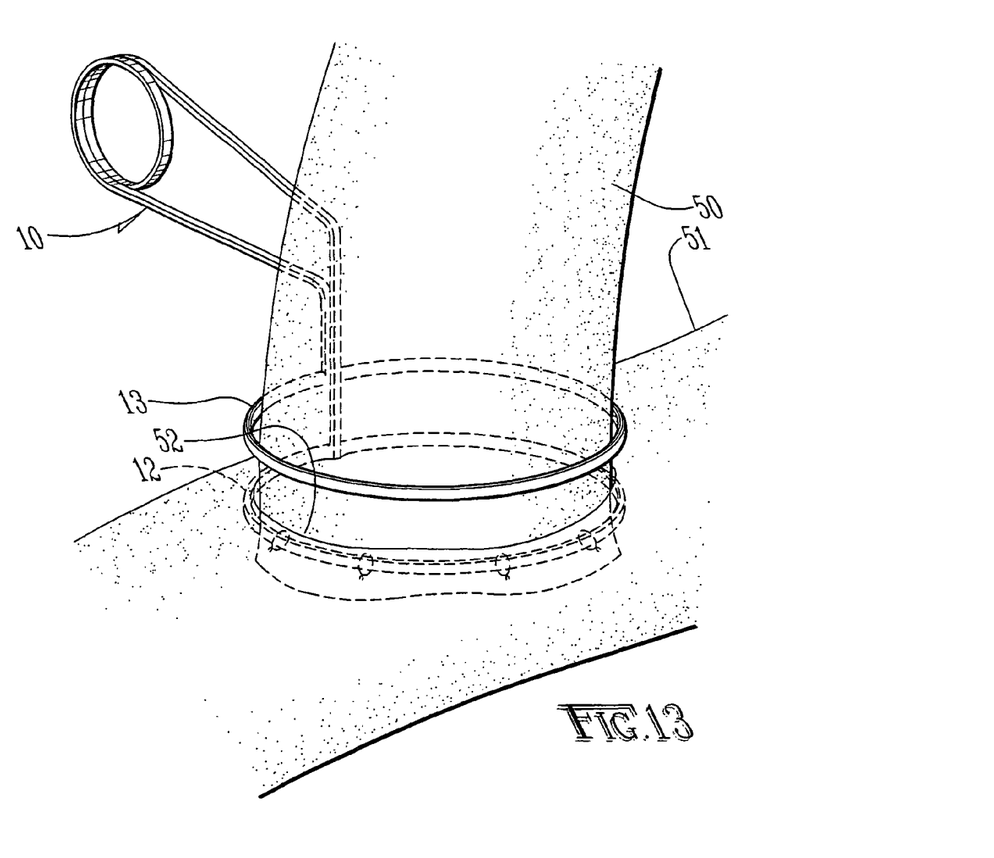

As shown in FIGS. 12-15, the clip 10 may be used to form an anastomosis by attaching a graft vessel 50 to a recipient vessel 51. As shown in FIG. 12, one end of the graft vessel 50 is inserted inside the two rings 12, 13 and an edge of the open end of the graft vessel 50 is sutured to the lower ring 12 while the clip 10 is held open to allow such suturing. A hole 52 (called an "arteriotomy") is made in the recipient vessel 51 that is smaller than the diameter of the rings 12, 13. As shown in FIG. 13, the lower ring 12 holding the open end of the graft vessel 50 is inserted into the hole 52 in the recipient vessel 51 while the clip 10 is held open so that the edge of the hole 52 is positioned between the two rings 12, 13. A shown in FIGS. 14 and 15, the clip 10 is then closed to catch the edge of the hole 52 in the recipient vessel 51 between the two rings 12, 13 as they are closed tightly and the anastomosis is thereby completed. The graft vessel 50 can be a vein or an artery (veins are preferred as having less thickness), either autologous or heterologous, or the graft vessel 50 can be made of a synthetic material. In the later case the graft vessel 50 may be attached to the lower ring 12 during the process of manufacturing the dip 10.

Figure 20:
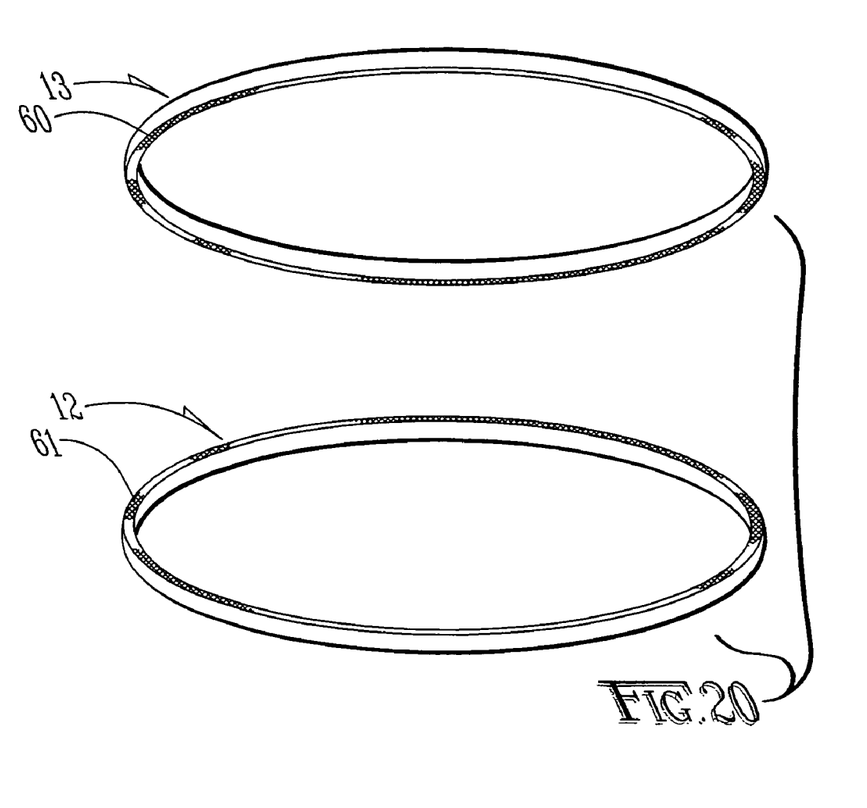
FIG. 20 is a perspective view of the upper and lower rings with their respective inner surfaces roughened.

To ensure a firm grasp of the rings 12, 13 on the walls of the recipient vessel 52, the lower surface of the upper ring 13 and the upper surface of the lower ring 12, i.e., the surface of each ring 12, 13 facing the other ring, may be provided with a rough surface 60, 61 as shown in FIG. 20. The surface may be roughened by any of various means known in the art, including parallel or crosshatched grooves. Alternatively, the inner surface of one ring may be provided with spines (not shown) that fit into complementary holes (not shown) on the facing surface of the other rings.

Figure 16:
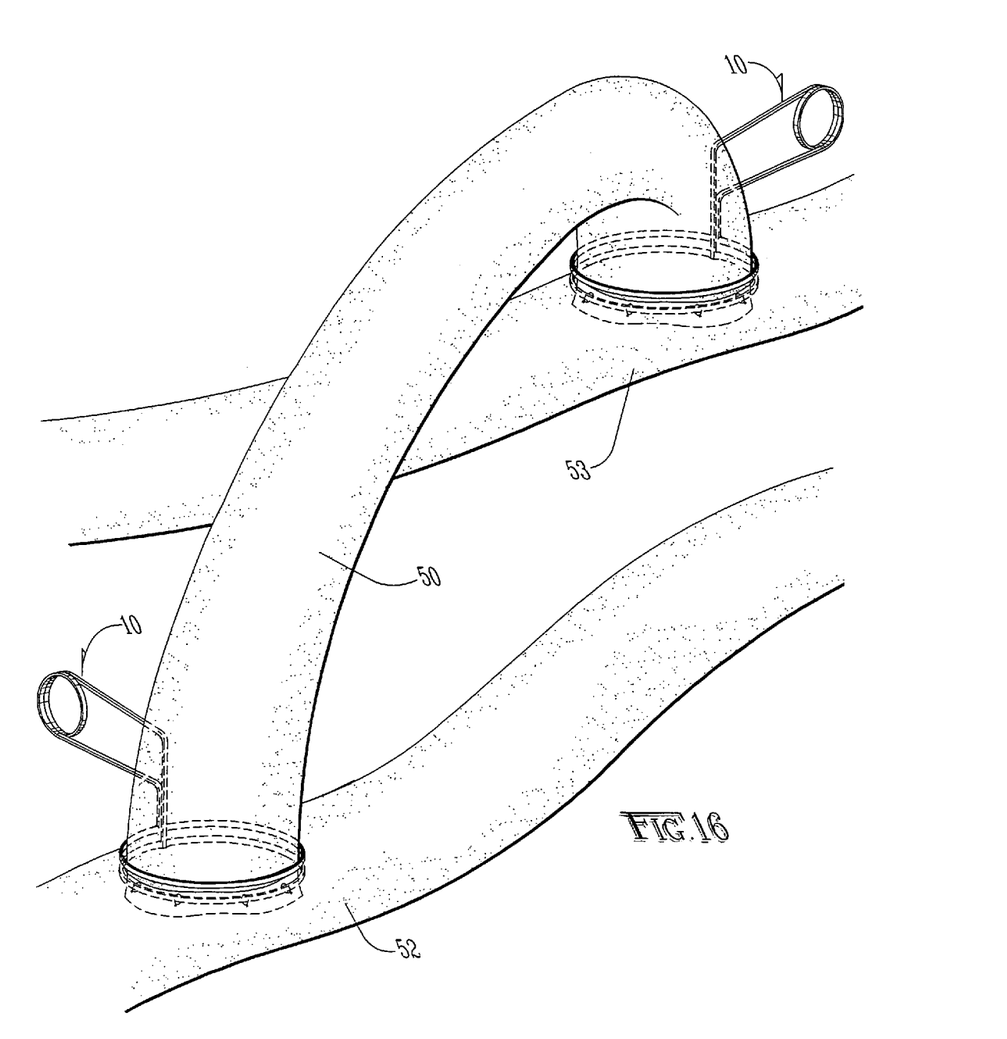
FIG. 16 is an elevation view of two clips being employed to attach a graft vessel between a donor vessel and a recipient vessel.
Figure 22:
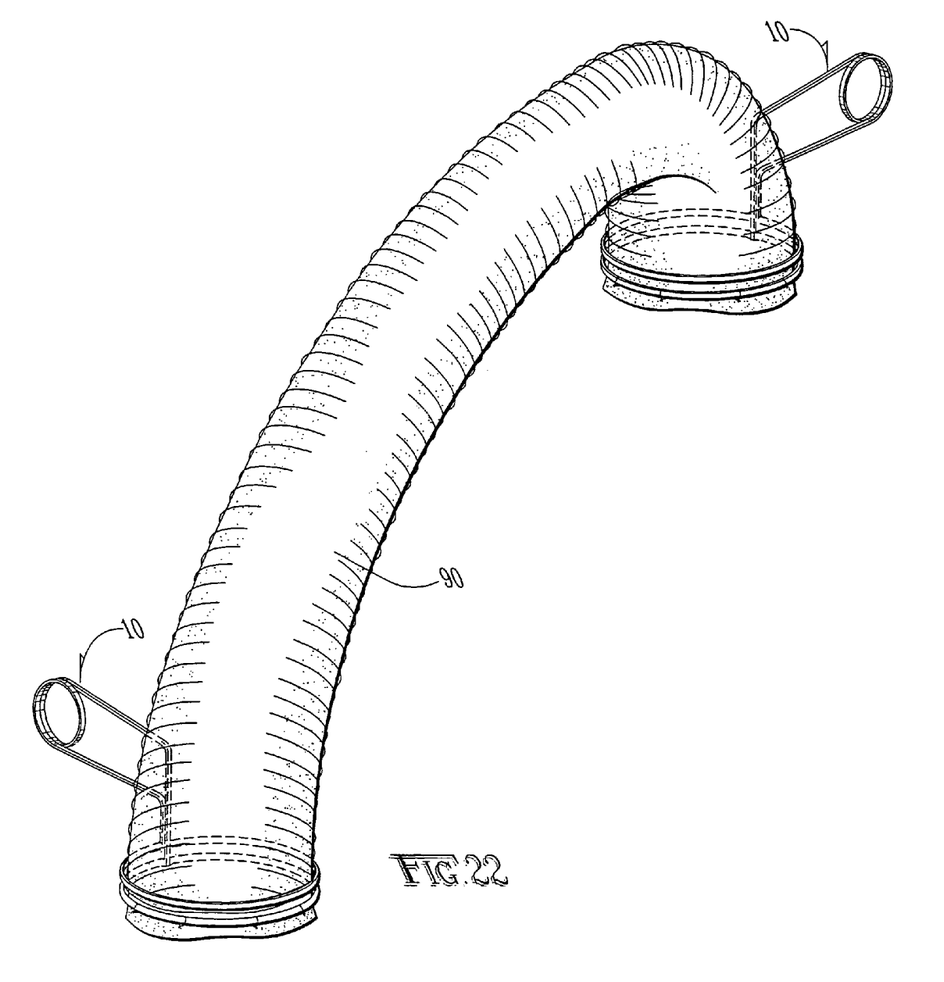
FIG. 22 is an elevation view similar to that of FIG. 16 showing a graft with corrugations that allow it to be stretched to a desirable length between a donor vessel and a recipient vessel.

With reference to FIG. 16, a clip 10 may be attached as described above to each end of a graft vessel 50 so that the graft vessel 50 may be connected between a donor vessel 53 and a recipient vessel 52. FIG. 22 shows an alternative version with a corrugated graft 90 that may be stretched to a desirable length between a donor vessel 53 and a recipient vessel 52. This avoids placing any force on the graft between the donor and recipient vessels and allows various maneuvers while applying and attaching the clips to the vessels. Such a corrugated form is well known from vascular grafts made of TEFLON for major vessels such as the aorta. The graft 50, 90 may be made in different sizes, including different diameters corresponding to the sizes and diameters of the rings 12, 13. The graft 50, 90 may also be made in different lengths.

Figure 17:
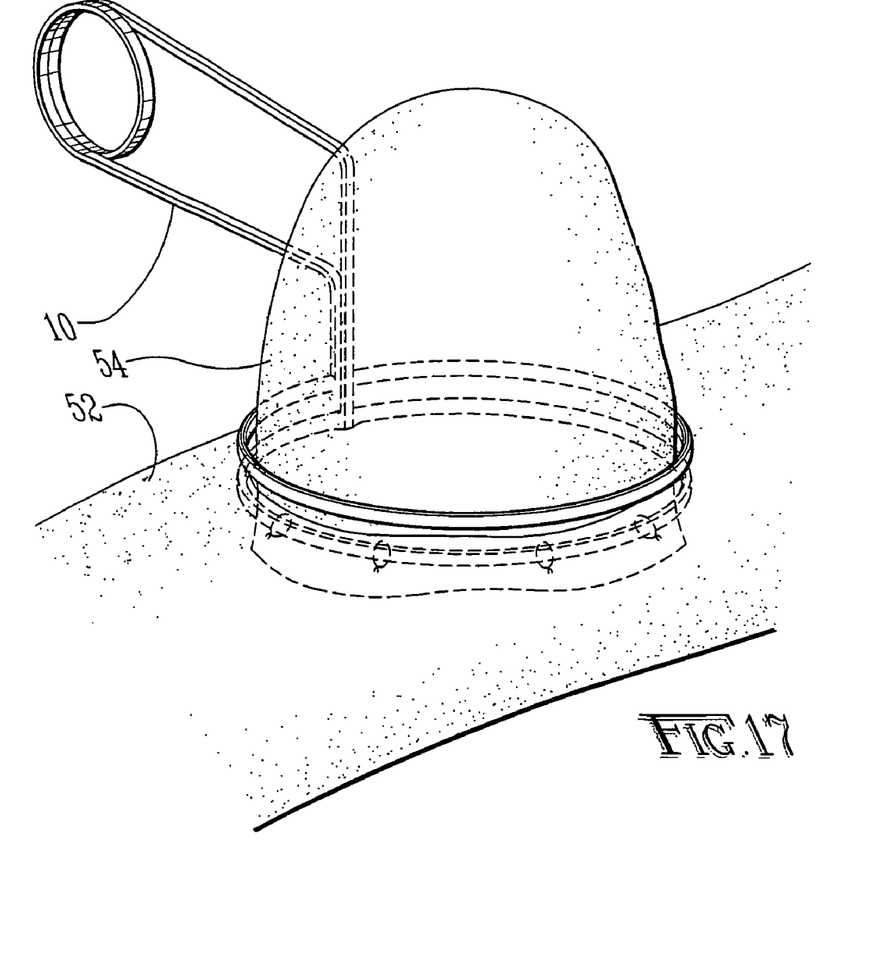
FIG. 17 is an elevation view of a clip being employed to attach an artificial aneurysm to a recipient vessel for surgical training purposes.

In an alternative embodiment illustrated in FIG. 17, instead of a graft vessel 50, an artificial aneurysm 54 may be attached to the lower ring 12 of the clip 10 as described above so that the artificial aneurysm 54 may be connected to a recipient vessel 52. This embodiment may be particularly useful in surgical training and may be used in conjunction with a training model such as the cadaver model described in U.S. Pat. No. 6,790,043 to the same inventor as the present invention.

The artificial aneurysm 54 may be applied in the teaching of different treatment modalities, such as coiling and endovascular treatment.

The present invention has been described above with reference to vascular anastomoses. However, the invention is not limited to anastomoses with the vascular system, but may be applied to any anastomoses between tubular or hollow structures in the human or animal body. Any use of the term "vascular anastomosis" or "vascular anastomoses" is intended to refer to any anastomoses except when the context clearly limits the meaning to anastomoses between structures in the vascular system.

The present invention has been described with reference to certain preferred and alternative embodiments that are intended to be exemplary only and not limiting to the full scope of the present invention as set forth in the appended claims.

What is claimed is:

1. A device for performing an anastomosis, comprising:
    an upper ring,
    a lower ring,
    wherein each of said upper ring and said lower ring comprise a shape selected from the group consisting of a closed circle and a closed ellipse,
    a handle connected to said upper ring and to said lower ring, and
    a graft vessel having a first end with an edge sutured to said lower ring;
    wherein said handle comprises a first arm and a second arm, said first arm connected to said lower ring and said second arm connected to said upper ring, and
    wherein said handle comprises a first offset segment connected between said first arm and said lower ring and a second offset segment connected between said second arm and said upper ring, and
    wherein said first offset segment is disposed to pass to the inside of said upper ring.

2. The device of claim 1, wherein said handle further comprises a resilient element whereby said upper ring and said lower ring are biased together.

3. The device of claim 2, wherein said resilient element comprises a spring.

4. The device of claim 1, where said upper ring comprises a roughened lower surface.

5. The device of claim 1, wherein said lower ring comprises a roughened upper surface.

6. The device of claim 1, where said upper ring and said lower ring are the same size and shape.

7. The device of claim 6, wherein said upper ring is characterized by a first maximum dimension, said lower ring is characterized by a second maximum dimension, and said first maximum dimension is the same as said second maximum dimension.

8. The device of claim 7, wherein said first maximum dimension and said second maximum dimension are at least 2 mm.

9. The device of claim 8, wherein said first maximum dimension and said second maximum dimension are no more than 2.5 cm.

10. The device of claim 1, wherein said graft vessel is an autologous graft.

11. The device of claim 1, wherein said graft vessel is a heterologous graft.

12. The device of claim 1, wherein said graft vessel comprises a synthetic material.

13. The device of claim 1 wherein said upper ring, said lower ring and said handle are integrally formed from a single segment of resilient material.

14. The device of claim 1 wherein said first arm and said second arm are pivotally connected at a pivot point.

15. The device of claim 1, further comprising a second device for performing an anastomosis having a second lower ring sutured to a second edge of an opposite end of said graft vessel.

* * * * *